(12) United States Patent
Hallen et al.

(10) Patent No.: US 6,217,594 B1
(45) Date of Patent: Apr. 17, 2001

(54) APPARATUS, SYSTEM AND METHOD FOR SECURING SCLERAL TISSUE

(75) Inventors: Paul Hallen, Sparks, MD (US); Dan Montzka, Tarpon Springs, FL (US); Gildo Fujii; Dante Pieramici, both of Baltimore, MD (US)

(73) Assignee: Retinalabs.com, Inc., Atlanta, GA (US)

( * ) Notice: Subject to any disclaimer, the term of this patent is extended or adjusted under 35 U.S.C. 154(b) by 0 days.

(21) Appl. No.: 09/425,283

(22) Filed: Oct. 21, 1999

(51) Int. Cl.$^7$ .................................................. A61B 17/08
(52) U.S. Cl. ............................................................ 606/157
(58) Field of Search ................................... 606/157, 151, 606/152, 221, 138, 139, 232, 233, 4, 6; 604/8, 10

(56) References Cited

U.S. PATENT DOCUMENTS

| 4,166,293 | * | 9/1979 | Anis . | |
|---|---|---|---|---|
| 5,722,982 | * | 3/1998 | Ferreira et al. | 606/151 |
| 5,916,224 | * | 6/1999 | Esplin | 606/151 |

* cited by examiner

*Primary Examiner*—Henry J. Recla
*Assistant Examiner*—Vikki Hoa Trinh
(74) *Attorney, Agent, or Firm*—Peter F. Corless; Edwards & Angell, LLP

(57) ABSTRACT

Devices, systems and methods are provided for the retention of scleral tissue during, and subsequent to, vitreoretinal surgical procedures. The devices include engagement portions for engaging circumferentially spaced exterior portions of the sclera attached respectively to opposite sides of a deformable portion. The systems include retention devices of the type just mentioned and emplacement devices adapted to hold the retention devices, deliver the retention devices to desired locations on the sclera of an eye, and to crimp the retention devices in place. The emplacement devices also may be capable of holding a plurality of retention devices for sequential location on the sclera without the need to remove the emplacement device from the vicinity of the sclera. Methods of the invention include steps required to locate and secure a retention device to scleral tissue. A preferred method includes the following steps. First, the system is provided. Then, retention device(s) are loaded onto/into the emplacement device. Thereafter, the retention device is located in a desired position relative to the scleral of an eye, followed by the activation of the emplacement device to secure scleral tissue between the engagement portions of the retention device.

13 Claims, 6 Drawing Sheets

APPARATUS, SYSTEM AND METHOD FOR SECURING SCLERAL TISSUE

BACKGROUND OF THE INVENTION

1. Field of the Invention

The present invention generally relates to medical devices and procedures involving the eye and eye surgery. In particular, the invention relates to medical apparatus, systems and methods for securing tissue during the course of, and after, surgical procedures involving the eye. Still more specifically, the present invention relates to medical apparatus, systems and methods for closing openings in scleral tissue formed during the course of vitreoretinal surgical procedures, and for securing folds formed in scleral tissue.

2. Background

Vitreoretinal surgical procedures for the treatment, or repair, of internal strictures of the eye are well known in the art. For example, the repair of holes or tears in the retina, and the re-attachment of detached retinas, now are fairly common surgical procedures. Similarly, the removal of the vitreous body (the clear, gel-like body that fills the interior of the eye) and its replacement with either another material or a prosthetic device is known. Numerous other examples of surgical procedures of this type will readily occur to those skilled in the art.

Typically, in each of these procedures, a plurality of incisions or "holes" (technically referred to as "sclerotomies") are formed in the sclera to provide access for surgical tools, cannulas and the like to the retina, to the vitreous body and to other internal ocular structures and tissues. Currently, manually placed and tied sutures are utilized both during the course of these surgical procedures, and thereafter. For example, manually placed and tied sutures typically are used for holding infusion cannulas, for securing and/or connecting tissue and otherwise during the surgical procedure, and thereafter to close the sclerotomies.

Manual suturing, however, is an inefficient, time consuming, and skill intensive practice. Further, it is well known that manually placed and tied sutures may tear out of tissue if excessive stress is placed thereon. Accordingly, since the tissue of the eye is subjected to substantial stress during most physical activities performed by a patient, including such simple exertions as coughing or sneezing, alternative apparatus, systems and methods for securing eye tissue would be desirable.

A specific representative example of a vitreoretinal surgical procedure wherein such alternative apparatus, systems and methods would be beneficial is commonly referred to as "Macular Translocation". This vitreoretinal surgical procedure has been recently developed as a substitute for the so-called "Retinal Translocation" procedure wherein the eye is literally disassembled by removal of the lens and the vitreous body, and by detaching the retina for translocation relative to the underlying tissue prior to re-assembly of the eye. These procedures are intended to treat conditions wherein the tissue underlying the macular (central vision) portion of the retina becomes diseased. Degenerative conditions of this sort may result in the photoreceptors of the macula portion of the retina adjacent to the underlying diseased tissue becoming non-functional over time. To avoid this result, the above procedures shift the position of the fovea (i.e., the central portion of the macular portion of the retina which is responsible for a person's sharpest vision) relative to the underlying inner surface of the sclera. This allows the fovea then to be reattached to healthier underlying tissue.

To accomplish this result, the Macular Translocation Procedure, which is less radical than the Retinal Translocation procedure, includes the following steps. First, sutures are placed in a horizontal mattress formation in an arc supero-temporally (i.e., just below the center of the eye, near the ear) on the outer surface of the sclera. These sutures typically are located in the same position relative to the eye regardless of the exact location of the diseased tissue. Then, at least the macula portion of the retina is intentionally detached from the underlying tissue. This usually is accomplished by performing a 3 port pars plana vitrectomy followed by the use of a subretinal infusion cannula and a balanced salt solution to create the desired retinal detachment. The pre-placed sutures are then tightened and tied off. This results in the creation of an inwardly extending fold in the sclera that effectively "shortens" the scleral diameter. Thereafter, an air bubble is formed inside the eye so that the excess length of the retina relative to the shortened underlying scleral surface is moved relative to the diseased tissue. Movement on the order of 1000 microns has been found to be adequate in most cases. Then, a partial air-fluid exchange is made. The natural fluid removal generated by the pigment epithelium and choroid allow the macula portion of the retina, which has been shifted relative to the underlying tissue by the deformation of the sclera and by the formation of the air bubble, to settle against, and reattach itself to, healthy tissue. Finally, several days after the surgical procedure, the diseased lesion is treated with standard laser photocoagulation.

The placement of the sutures in the macular translocation procedure is time consuming and, therefore, inefficient. It is also difficult to consistently predict the distance of scleral shortening that will result upon the tightening and tie off of the sutures. Further, the skill level required to place and to manipulate the sutures without causing extraneous damage to the eye, or surrounding bodily structures, is high.

SUMMARY OF THE INVENTION

The invention includes simple, reliable and accurate apparatuses, systems and methods for non-manually securing scleral tissue during, and after, vitreoretinal surgical procedures.

The invention also includes non-manual apparatuses, systems and methods for permanently closing and securing scleral incisions, and for securing folds in scleral tissue formed during macular translocation procedures.

In addition, the invention provides apparatuses, systems and methods adapted to form the scleral folds of the macular translocation procedure such that those folds extend exteriorly of the sclera, rather than interiorly thereof. Such outwardly extending folds would be superior to the current inwardly extending folds because the interior of the shortened scleral thereby would be made smooth. This would not only facilitate retinal reattachment, but also would result in a reattached retinal surface providing less distorted visual perceptions to the patient.

Such aspects of the present invention generally are accomplished by the provision of scleral tissue securing apparatuses, scleral tissue securing apparatus delivery and attachment tools and methods for using the same.

More particularly, the present invention contemplates numerous scleral tissue securing apparatuses. Each of these apparatuses includes tissue engagement portions adapted to respectively engage spaced, substantially circumferential exterior portions of the sclera of an eye. Further, the tissue engaging portions are connected by at least one deformable portion which, when deformed, acts to retain the tissue engagement portions in close proximity to one another such that two layers of scleral tissue can be secured therebetween.

In the preferred embodiments, the apparatus may take any one of several forms. Specifically, as will be discussed in further detail below, the apparatus may be a deformable, generally U-shaped clip having inwardly extending tissue engagement flanges located at its free ends. It also may be an elongated clamp having a deformable, generally U-shaped cross-section and inwardly extending tissue engagement flanges located at its free edges. Further, it may be an elongate clamp or belt adapted to be wound upon itself and made of a material that will allow it to be crimped in place. Still further, it may be a flexible band having preformed sets of holes located adjacent to each of its ends to be tied in position by sutures threaded through the preformed holes. In addition, it may be a pair of pins and at least one length of suture.

Also as will appear more fully below, the preferred system of the invention is contemplated to include a delivery and affixation device for use with an associated securing apparatus The method of the invention is contemplated to include the method of using the above-mentioned preferred system embodiments of the invention, and will become more apparent to those skilled in the art below.

BRIEF DESCRIPTION OF THE DRAWINGS

These and other objects, aspects, features and advantages of the present invention will become apparent from the following detailed description of its preferred embodiments. This description is provided with reference to the appended drawings in which like reference numerals are used to refer to like elements throughout, and in which.

DETAILED DESCRIPTION OF THE INVENTION

Figure 1:
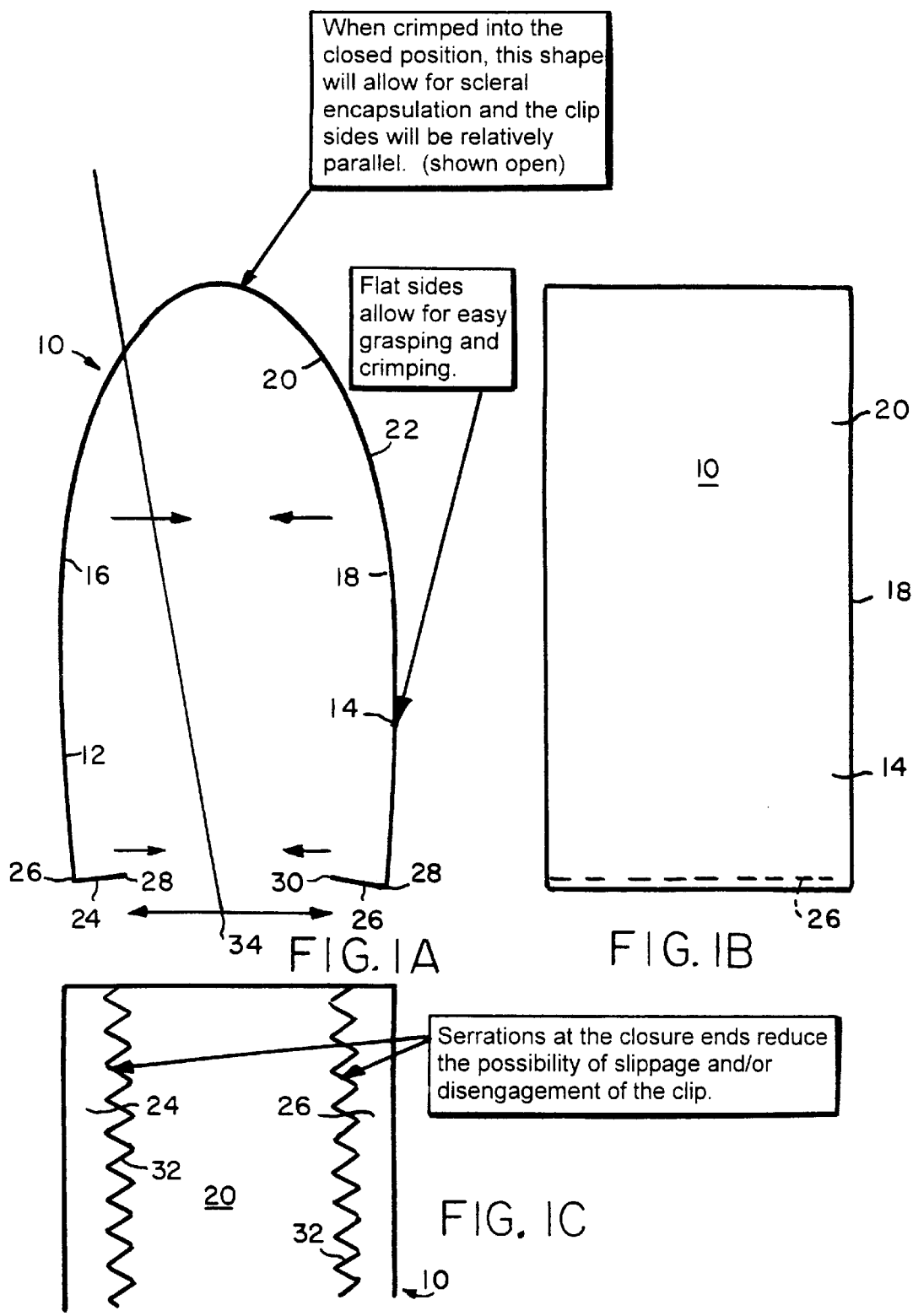
FIG. 1A is an illustrative front view of a scleral clip in accordance with the present invention.
FIG. 1B is an illustrative side view of the scleral clip in accordance with the embodiment of present invention shown in FIG. 1A.
FIG. 1C is an illustrative bottom view of the scleral clip in accordance with the embodiment of present invention shown in FIGS. 1A and 1B.

Referring now to the drawings, and particularly to FIGS. 1A–1C, it will be seen that one preferred embodiment of the apparatus of the present invention is a substantially U-shaped clip, generally indicated at 10. More specifically, the clip 10 includes a pair of substantially parallel wall portions 12 and 14 connected along adjacent edge portions 16 and 18 by a base portion 20 so as to form a generally U-shaped body 22. In addition, flange portions 24 and 26 extend inwardly from the adjacent free end edge portions 26 and 28 of generally U-shaped body 22 at acute angles to the wall portions 12 and 14, respectively. Wall portions 12 and 14, and flange portions 24 and 26 are each substantially flat, while base portion 20 is substantially parabolic in transverse cross-section. Further, the facing inner edges 28 and 30 of flange portions 24 and 26 may be provided with serrations or other tissue grasping protrusions 32, if desired.

The clip is suitably formed of e.g. a malleable material having an elastic limit, such as stainless steel, tantalum, titanium or various types of plastic, or other synthetic materials. Other suitable materials will be apparent based on the present disclosure and/or can be identified by simple testing. In addition, the clip is suitably dimensioned such that the throat dimension 34 between the inner edges 28 and 30 of flange portions 24 and 26 is slightly larger than the width of a desired scleral fold. Similarly, the throat dimension may have a width slightly larger than the combined thicknesses of the edges of a sclerotomy that is to be secured therewith. Further, the interior of the clip may be sized to surround the outer surface of a scleral fold of a predetermined height.

Accordingly, as will be described in greater detail below, the wall portions 12 and 14 may be forced toward one another. This will cause the parabolically shaped base portion 20 to bend outwardly. Thereafter, once the elastic limit of the material of the clip is reached, the clip will collapse, inwardly upon itself. This inward collapse will occur primarily in the base portion 20 and be such that the clip 10 assumes a deformed shape in which the inner edges 28 and 30 of flange portions 24 and 26 are retained in close proximity to one another (see FIG. 9).

Figure 2:
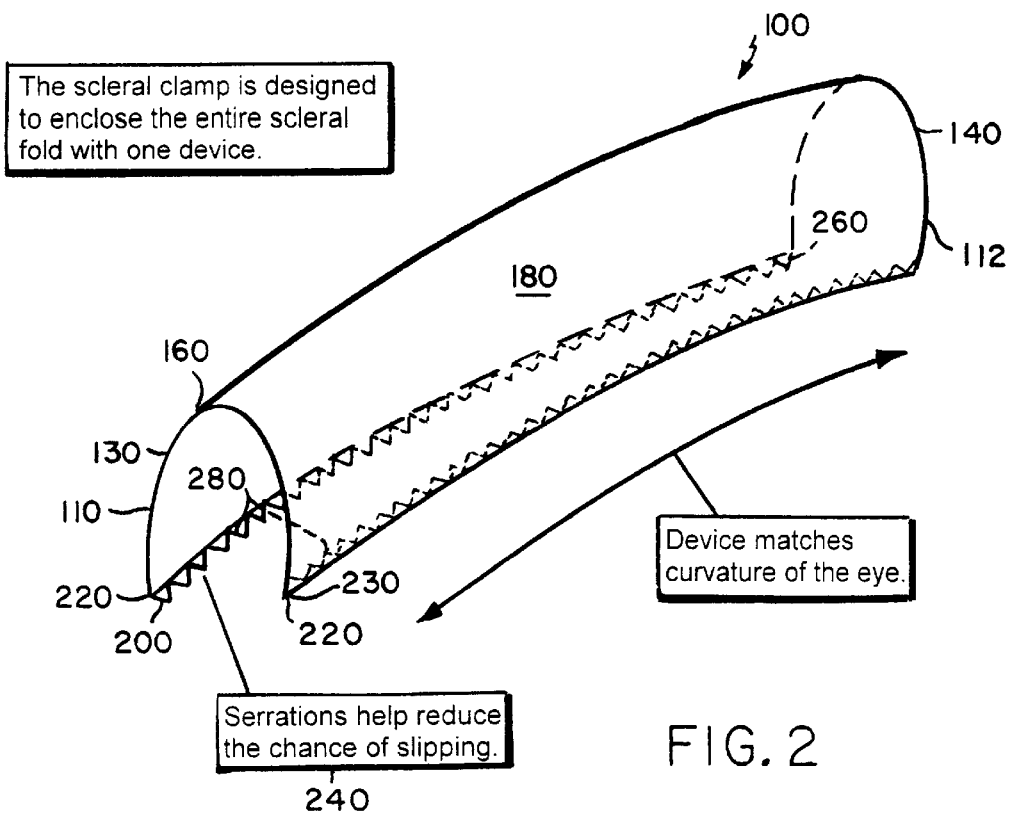
FIG. 2 is an illustrative side perspective view of a scleral clamp in accordance with the present invention.

In another preferred embodiment of the invention illustratively shown in FIG. 2, the apparatus of the present invention is a substantially U-shaped clamp, generally indicated at 100. Clamp 100 is very similar to clip 10. More specifically, clamp 100 includes a pair of substantially parallel wall portions 110 and 120 connected along adjacent edge portions 130 and 140 by a base portion 160 so as to form an elongate body 180 having a generally U-shaped transverse cross-section. In addition, flange portions 200 and 210 extend inwardly from the adjacent free end edge portions 220 and 230 of generally U-shaped body 180 at acute angles to the wall portions 110 and 120, respectively. Wall portions 110 and 120, and flange portions 200 and 210 are each substantially flat, while base portion 160 is substantially parabolic in transverse cross-section. Further, the facing inner edges 240 and 260 of flange portions 210 and 220 may be provided with serrations or other tissue grasping protrusions 280, if desired.

The clamp 100 is formed of a malleable material having an elastic limit such as stainless steel, tantalum, titanium or various types of plastic. In addition, the clamp 100 is dimensioned such that the throat dimension 240 between the inner edges 280 of flange portions 200 and 210 is slightly larger than the width of a scleral fold or the edges of a sclerotomy which is to be secure therewith. Accordingly, as will be described in greater detail below, the wall portions 110 and 112 may be forced toward one another. This will cause the parabolically shaped base portion 160 to bend, and thereafter to collapse, inwardly upon itself. Thus, clamp 100 will assume a deformed shape in which the inner edges 240 and 260 of flange portions 200 and 210 will be retained in close proximity to one another. In addition, it may be found to be beneficial to form the clamp in such a way that at least the free end edge portions 220 and 230 form an arc. In the preferred embodiment, this arc is generally complementary to the outer surface of the scleral tissue against which the outer edges of the U-shaped clamp are to be placed in use. This alternative will ensure that the best possible engagement of the scleral tissue layers to be grasped and retained by the clamp will be achieved in use. Further details of this alternative will become apparent to those skilled in the art as the present discussion proceeds.

Figure 3:
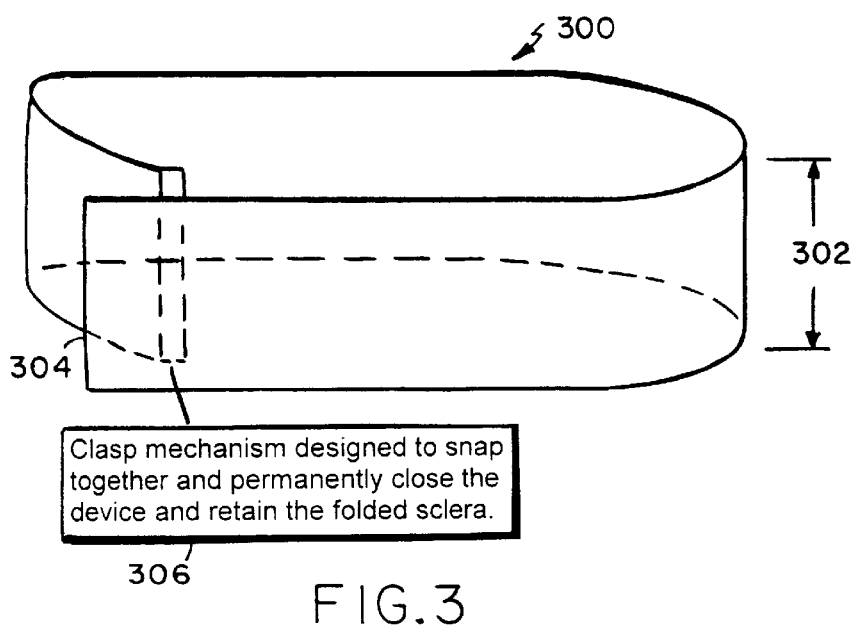
FIG. 3 is an illustrative perspective view of a scleral clasp in accordance with the present invention.

In yet another preferred embodiment, illustratively shown in FIG. 3, the apparatus may include an elongate clasp or belt, generally indicated at 300. This clasp or belt 300 is formed of a material similar to that of the clip 10 or the clamp 100 discussed above. Further, it is dimensioned such that it may be wound upon itself around a fold of scleral tissue. More particularly, the clamp or belt 300 has a width dimension 302 equal to, or less than, the height of a fold of scleral tissue that it is to retain. Further, it has a length that exceeds the peripheral length of the fold of scleral tissue that it is to retain. Thus, as will become more apparent below, one end 304 of the clasp or belt 300 is placed against a side of a scleral fold, and thereafter the clasp or belt is tightly wound around the periphery if the scleral fold. Then, the clasp 300 is crimped to secure it in place, and excess portions of the clamp or belt are removed.

Figure 4:
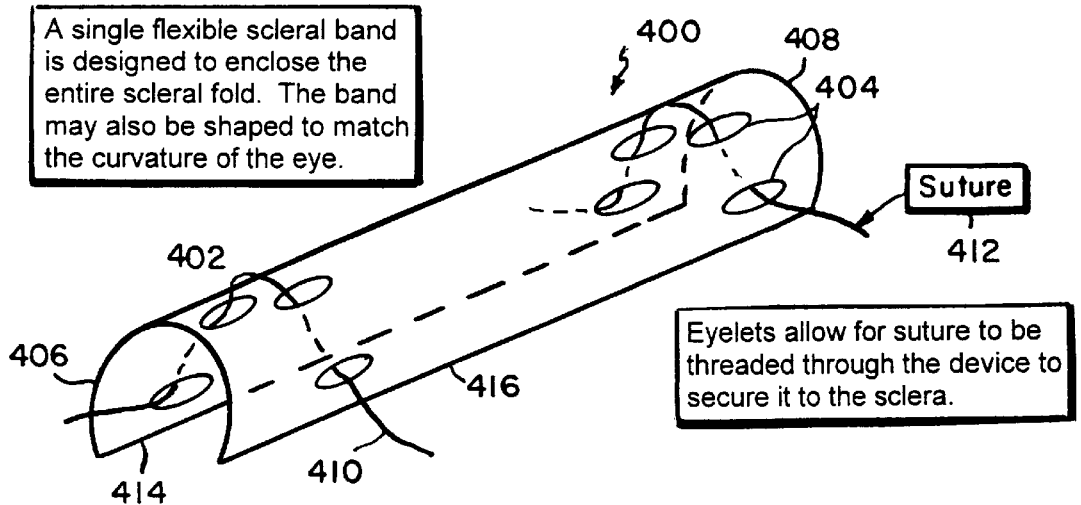
FIG. 4 is an illustrative perspective view of a scleral band and associated sutures in accordance with the present invention.
Figure 12:
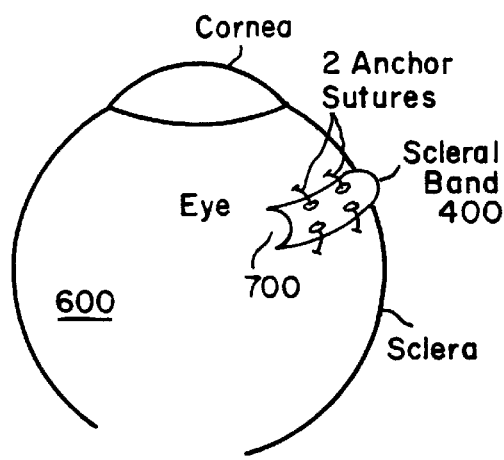
FIG. 12 is an illustrative view showing a band and suture apparatus as shown in FIG. 4 securing a scleral fold in place.
Figure 13:
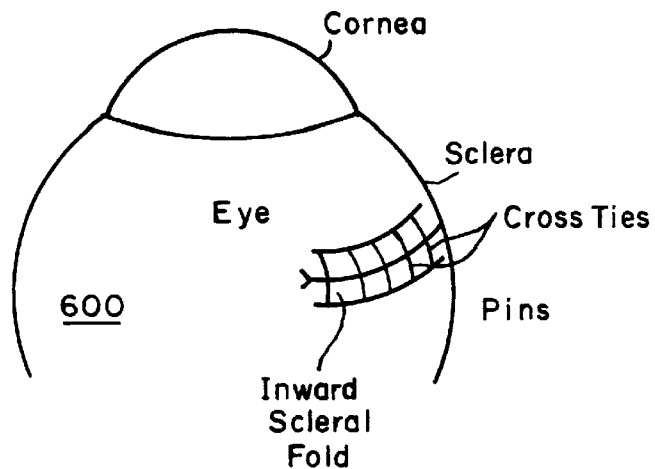
FIG. 13 is an illustrative view showing a pin and suture structure as shown in FIG. 5 holding an inwardly projecting scleral fold in place.

In still another embodiment, illustratively shown in FIG. 4, the apparatus includes an elongate, flexible band 400 having preformed sets of holes 402 and 404 located adjacent to each of its ends 406 and 408, respectively. The band is foldable over an outwardly extending scleral fold (FIG. 12), and adapted to be tied in position by sutures 410 and 412 threaded through the preformed holes. In this embodiment as well, the elongate edges 414 and 416 of the band 400 which are to rest against the outer surface of the sclera define an arc complementary to that of the exterior scleral surface. A preferred material for this embodiment of the invention is flexible silicon rubber or the like.

Figure 5:
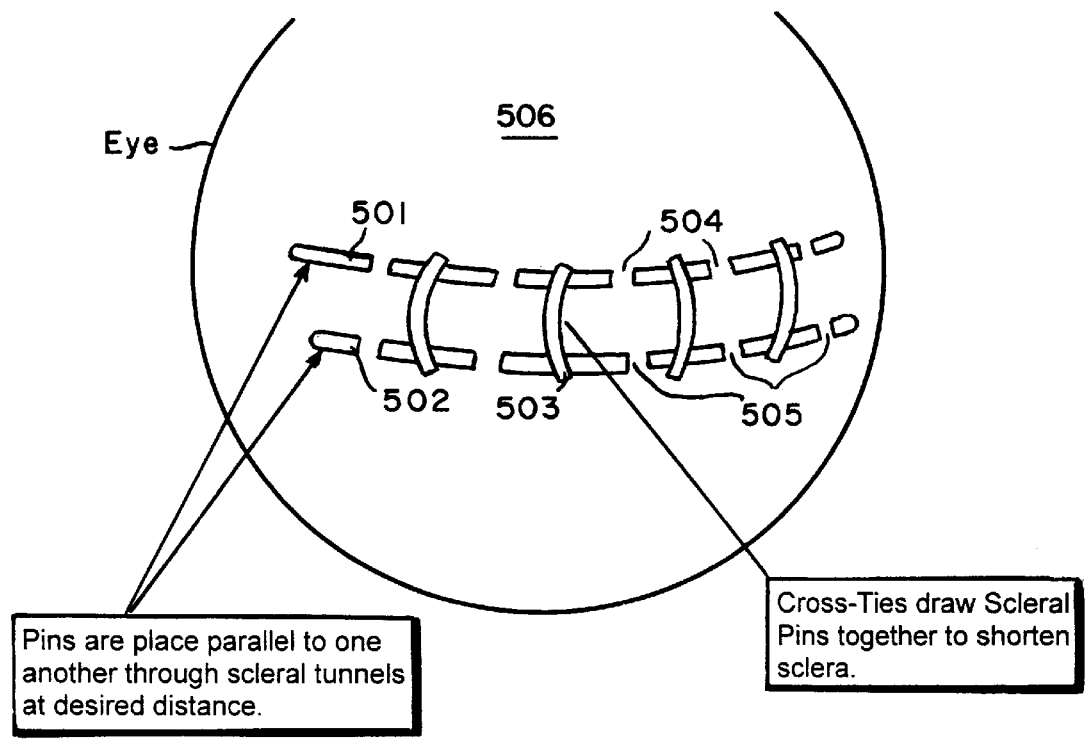
FIG. 5 is an illustrative view showing a pin and suture embodiment of the apparatus of the present invention attached to the sclera of an eye.

In still a further preferred embodiment of the present invention, illustratively shown in FIG. 5, a pair of pins 501 and 502 and at least one length of suture 503 are provided. The pins 501 and 502 are adapted to be threaded through a group of substantially aligned scleral tunnels, 504 and 505, respectively, that are spaced from one another on the outer surface of the sclera 506. The suture 503 ties the pins together as will be discussed further below. Further, it will be clear to those skilled in the art that the pins 501 and 502 should be formed so as to define an arc complementary to the portion of the sclera in which they are to be placed.

Figure 8:
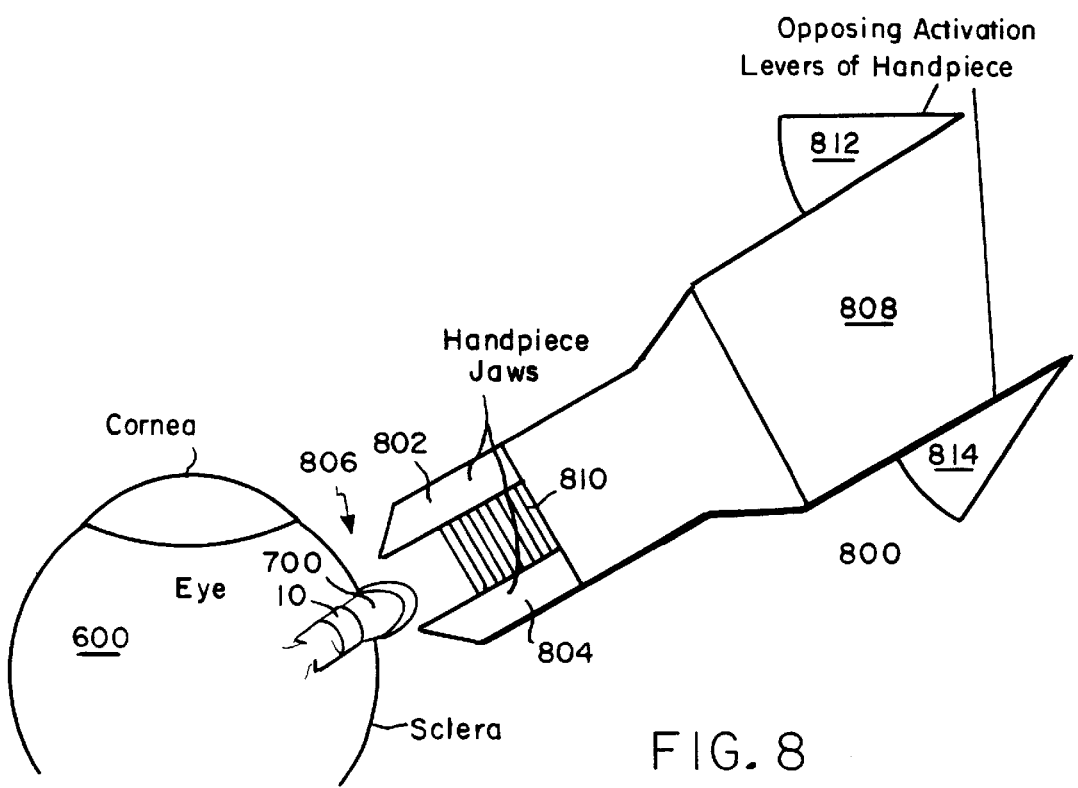
FIG. 8 is an illustrative view similar to FIG. 7 showing a delivery and attachment device locating a clip as shown in FIGS. 1A–1C over a fold in the scleral wall.

The preferred system of the invention includes a delivery and affixation device 800, best seen in FIG. 8. This device is primarily designed for use with either the clip 10 or the clamp 100 embodiments of the apparatus discussed above. The device 800 is hand held, and includes a pair of opposing jaws 802 and 804 at its distal end 806 for crimping the deformable apparatus of this invention once it is properly placed relative to opposing sides of a scleral fold or a sclerotomy. In the embodiment illustratively depicted in FIG. 8, device 800 includes an elongate, substantially cylindrical, hollow shaft 808. The shaft 808 is designed to carry a plurality of clips, representatively shown at 810, in its interior for sequential positioning between jaws 802 and 804 and location relative to scleral tissue. The device 800 also includes opposing external activation levers 812 and 814 connected to jaws 802 and 804, respectively, within the shaft 808. Accordingly, a clip 10 or a clamp 100 may be disposed over a fold or multiple layers of scleral tissue by the device 800. Thereafter, the clip or clamp may be crimped in place by the application of inward pressure to levers 812 and 814 to force jaws 802 and 804 together in a tweezers-like action. Hence, the retention of multiple layers of scleral tissue may be made a simple, efficient and safe procedure.

The method of the invention includes the various steps involved in using the apparatuses and system described above. In particular, the method addresses two goals. First, it provides a way of efficiently, reliably and safely closing sclerotomies after the completion of vitreoretinal surgical procedures. Second, it provides a way to simplify, and in some instances improve, the macular translocation procedure discussed above.

Figure 6:
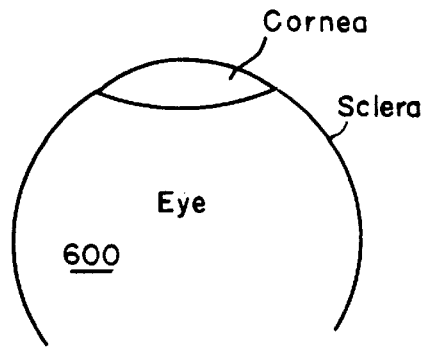
FIG. 6 is an illustrative side view of an eye.
Figure 14:
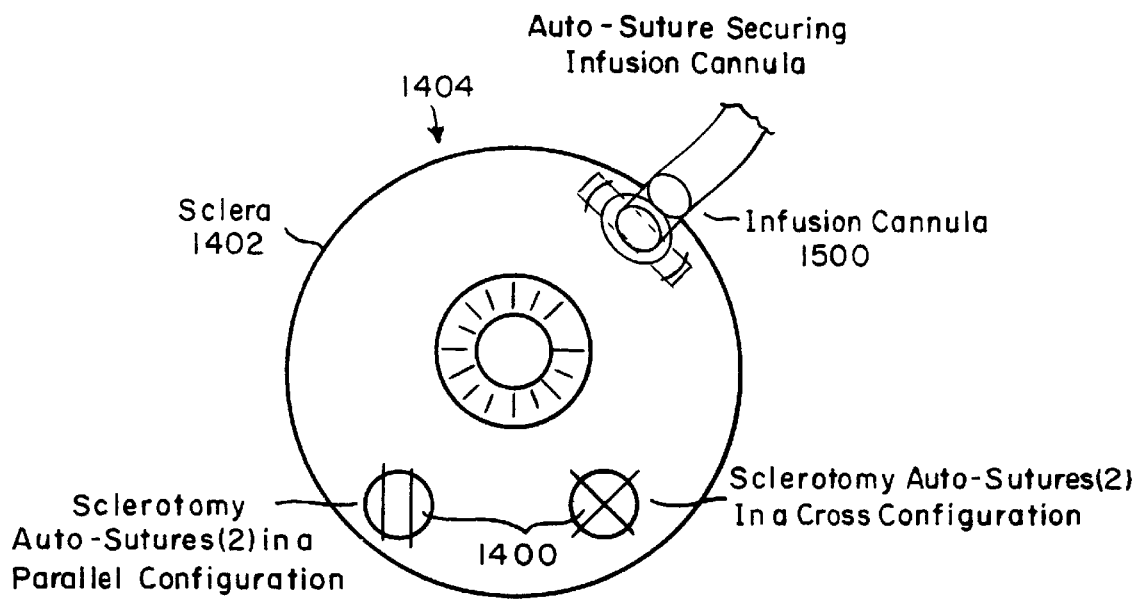
FIG. 14 is an illustrative view of the sclera and iris of an eye wherein sclerotomies have been closed and an infusion cannula has been attached to the sclera of the eye with clips in accordance with the present invention.

Referring now specifically to FIGS. 6–13, an illustrative side view of an eye, generally indicated at 600 is shown in FIG. 6 prior to the performance of vitreoretinal surgery thereon. As mentioned above, and well understood by those skilled in the art, vitreoretinal surgery typically includes the formation of sclerotomies 1400 at spaced locations about the sclera 1402 of the eye 1404, as generally shown in FIG. 14. The purpose of these sclerotomies is to provide the surgeon with access to the vitreous body, the retina and other interior portions of the eye during vitreoretinal surgical procedures.

This access is usually accomplished by means of cannulas and/or other surgical instruments (not shown). These surgical instruments are commonly of the type including an elongate shaft having a tissue manipulation device at its distal end. Also, a handle portion commonly is located at the proximal end of the shaft, and activation apparatus generally extends from the handle through the shaft to its distal end. This structure permits the surgeon to manipulate and/or to remove tissue within the eye from a location exterior of the eye. Hence, it will be understood the sclerotomies generally are short incisions or "holes" extending through the scleral tissue of the eye. It will also be appreciated that regardless of their size, these sclerotomies must be closed at the conclusion of the surgical procedure. Similarly, in the macular translocation procedure described above, the fold formed in the scleral tissue must be securely held together at the conclusion of the surgical procedure so that the foveal portion of the macula of the retina can reattach itself to healthy underlying tissue.

To accomplish these goals, the method of the present invention provides a scleral tissue securing apparatus and a positioning and crimping apparatus substantially as discussed hereinabove. The tissue securing apparatus is placed between the jaws at the distal end of the positioning device such that its open end faces distally (or in some cases transversely) relative to the longitudinal axis of the tool.

Then, using a forceps or similar surgical instrument, the scleral tissue is grasped to form the desired outwardly projecting fold or to draw the edges of a sclerotomy together. Then, the open end of the securing apparatus is placed against the outer surface of the sclera such that it straddles the outwardly projecting tissue. In this position the respective tissue engaging portions of the apparatus engage the scleral tissue at predetermined, spaced-apart locations. These locations are generally selected to be on opposite sides of a sclerotomy, or tissue fold, according to the specific application. Then, the jaws of the positioning tool are squeezed together to crimp the securing apparatus in place. As this occurs, the scleral tissue between the engagement portions is fixed in place by the deformation of the securing apparatus.

This procedure has several advantages over the current practice of manually suturing scleral tissue either to close sclerotomies, to create and secure localized folds in scleral tissue, or to temporarily secure surgical devices such as infusion cannulas in a desired position during the course of a vitreoretinal surgical procedure. It is faster than manual suturing, and requires less skill. Furthermore, it provides for either temporary or permanent scleral tissue retention. In addition, the dimensions of the retention apparatuses may be preselected thereby reducing the difficulty of determining the size of a scleral fold to be formed and allowing a sclerotomy to be closed along a line essentially flush with the adjacent scleral tissue. Incidentally as well, the scleral fold resulting from the use of the present apparatus, system and method usually results in the formation of an outwardly, instead of an inwardly, projecting fold of scleral tissue. This results in a more uniform surface for retinal reattachment.

Figure 7:
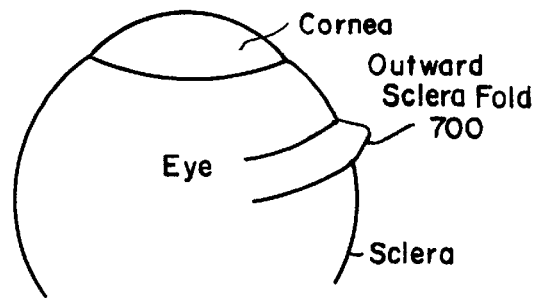
FIG. 7 is an illustrative side view of the eye shown in FIG. 6 wherein an outwardly projecting fold has been formed in the scleral wall.

Accordingly, as is representatively shown in FIGS. 14 and 7, respectively, a vitrosurgical procedure on the eye will result in sclerotomies 1400, and in some cases scleral tissue folds, such as that generally indicated at 700. The outwardly projecting folds and/or scelotomy edges typically are manually formed utilizing surgical instruments.

Figure 9:
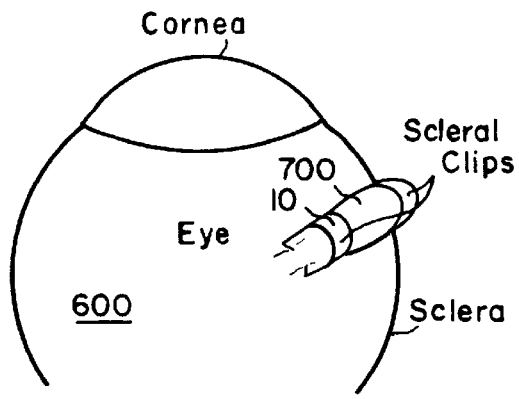
FIG. 9 is an illustrative view showing a clip as shown in FIGS. 1A–1C securing a scleral fold in place.
Figure 10:
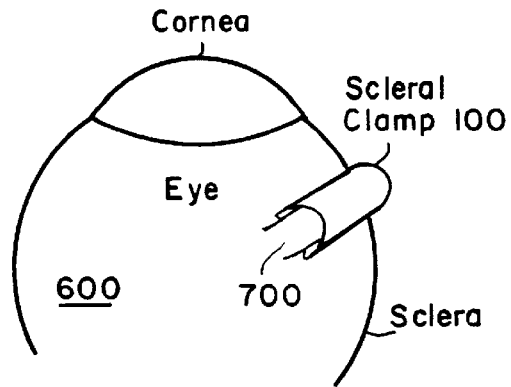
FIG. 10 is an illustrative view showing a scleral clamp as shown in FIG. 2 securing a scleral fold in place.
Figure 11:
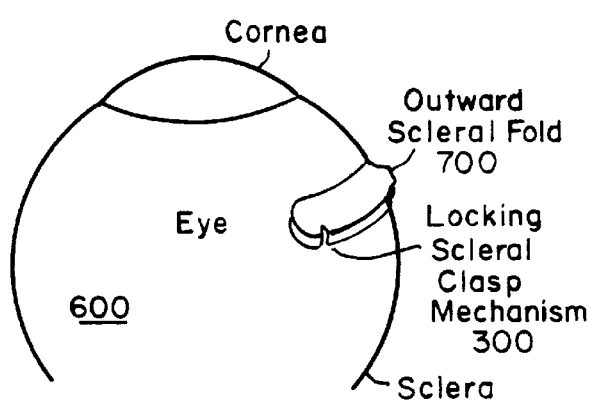
FIG. 11 is an illustrative view showing a clasp as shown in FIG. 3 securing a scleral fold in place.

More specifically, as is shown in FIG. 8, a scleral tissue retention apparatus of predetermined dimensions is located between the open jaws of the positioning tool. The positioning tool then is used to locate the retention apparatus, in this case a clip, over the outwardly projection scleral tissue. The jaws of the positioning tool then are squeezed together so as to crimp the retention apparatus around the outwardly projecting tissue, and to retain that outward projection in place (FIG. 9). Of course, if desired, one free edge of the clip might engage a flange or other holding member projecting outwardly from an infusion cannula 1500 or the like while the other free edge engaged scleral tissue (FIG. 14). In the latter case, crimping of the clip by squeezing the jaws of the positioning tool together would effectively secure the cannula or the like in a desired position during surgery. In the latter case the cannula or the like may be removed at the end of the surgical procedure by forcing the crimped edges of the clip away from one another so as thereby to release the cannula or the like from the scleral tissue.

It is contemplated that in the case of the clip, several (e.g., 5 to 6) clips will have to be placed along the length of the folded scleral tissue in order to securely maintain the desired configuration. To accomplish this, a single clip positioning and crimping device may be used as discussed above. It is contemplated, however, that a positioning and crimping device adapted to transport a plurality of clips internally, and to sequentially supply the same to the movable jaws might also be used as mentioned hereinabove.

The method of using the clamp 100 (FIG. 10) is essentially the same as that of using the clips 10. In this case, however, a single device would encapsulate the entire outwardly extending tissue projection 700, and the edges adapted to contact the adjacent scleral surface would be provided with an arc shape complementary to the curvature of the sclera. In this case as well, the positioning and crimping device might, or might not, include jaws designed to gasp the entire width of the scleral tissue retainer. If not, the clamp would be grasped by a positioning and crimping device such as that discussed with reference to the clip alternative during the positioning step. Thereafter, the jaws of the positioning device would be squeezed together at multiple locations along the length of the clamp to secure the device in place.

In the use of the clasp 300 (FIG. 11), the method requires that the outwardly projecting scleral tissue be formed prior to the application of the scleral tissue retention apparatus. Specifically, an end 304 of the clasp 300 is placed against a side of the outwardly projecting scleral tissue 700. Then, the clasp is wound around the projecting scleral tissue substantially entirely covering its outer side surface, but leaving its outwardmost portion exposed to minimize irritation. The jaws of a crimping tool then are placed around the clasp and squeezed together so as to lock the clasp in position. Alternatively, if desired, a mechanical locking mechanism 306 may be provided at one end of the clasp. In such a case, the mechanical lock may be the only element crimped by the positioning tool, or the lock may be a self-actuating one-way buckle or the like.

Alternatively, the clasp might be wound only part way around the outwardly projecting scleral tissue while leaving the outermost portion thereof and both of its shorter edges exposed. In this position, the clasp would then be crimped to retain the outwardly projecting scleral tissue in place. Further, the inner surface of the clasp may be provided with barbs or other tissue engaging projections (not shown) to prevent tissue slippage by virtue of their being driven into the projecting scleral tissue during crimping. Still further, an elongate edge of the clasp may be provided with an adjacent pair of arc shapes complementary to the curvature of the scleral surface. Thus, during the course of winding the clasp around the projecting scleral tissue, a close fit to the adjoining sclera surface may be obtained.

The method of use of the remaining two embodiments of the invention discussed above is somewhat different. Thus, in the case of the band 400 (FIGS. 4 and 12), the device is not rigid. Therefore, a positioning tool as discussed above cannot position it. Rather, in this case, the band 400 is folded over the outwardly projecting scleral tissue 700 so as to encapsulate is entire length. Its opposing elongate edges also may be arc shaped so as to fit complementarily against the adjoining scleral surface. The device is held in place by lengths of suture 410 and 412 threaded respectively through holes 402 and 404 located adjacent the shorter edges 406 and 408 of the band and into and out of the outwardly projecting scleral tissue 700. The holding strength of the band utilized in this method is not as great as that of the clip 10 or the clamp 100 discussed above. However, the eye is subject to substantial strain from the most mundane seeming physical activity of the patient. It is believed, therefore, that in some cases it may be preferable to give up the rigidity of the clamp in favor of the more flexible and pliable construction of the band.

Finally, method utilizing the pin and suture (FIGS. 5 and 13) is the closest to the manual suturing which is the current norm. In this case, two opposing sets of circumferentially aligned scleral tunnels 504 and 505 are formed in the outer portion of the scleral tissue 506. These sets of scleral tunnels are aligned along opposing edges of the area corresponding to that covered by the mattress sutures in the conventional macular translocation procedure discussed above. A pin 501 or 502 is then threaded through each set of aligned scleral tunnels. Thereafter, lengths of suture 503 are used to connect the pins either perpendicularly across the gap between them, or at various angles. Then, at the appropriate point in the macular translocation procedure, after the retina has been intentionally detached, the sutures 503 are tightened and tied off. The result is an inwardly projecting scleral tissue fold, just as in the conventional procedure. However, the use of the pins in the scleral tunnels provides the advantage of a continuous line of contact with the scleral wall along the open ends of the scleral fold. Thus, the stress imparted to the eye by physical activity of the patient is distributed over a larger area, and there is less chance of the sutures being torn out of the tissue.

It is to be understood that the foregoing description of the preferred embodiments of the present invention has been presented herein by way of illustration only. Numerous variations, changes, modifications, alterations and the like, all within the scope of the present invention in its broadest aspects, will occur to those skilled in the art in view of the above specification and the appended drawings. Accordingly, it is intended that the present invention be limited only by the terms of the appended claims.

What is claimed is:

1. A scleral tissue retention device comprising:
    first and second engagement portions, each defining an edge complementarily curved relative to the exterior scleral surface and adapted to respectively engage first and second spaced, substantially circumferential, exterior areas of the sclera of an eye; and
    deformable retaining portion, connected on opposite sides thereof to said respective engagement portions, for holding said first and second engagement portions in close proximity to one another such that two layers of said sclera of said eye can be retained therebetween when the retaining portion has been deformed.

2. The scleral tissue retention device according to claim 1, wherein the retaining portion comprises a malleable, substantially U-shaped member, and said first and second engagement portions respectively comprise flanges extending inwardly from the respective open ends of said substantially U-shaped member.

3. The scleral tissue retention device according to claim 2, wherein each of said flanges is disposed at an angle of less than 90 degrees to the leg of said U-shaped member adjacent thereto.

4. The scleral tissue retention device according to claim 3, wherein the flanges define serrated inner edges adapted to engage sceral tissue.

5. The scleral tissue retention device according to claim 2, wherein the engagement portions comprise elongate members.

6. The scleral retention apparatus according to claim 1, wherein the apparatus is formed of one or more material selected from the group consisting of titanium, tantalum, stainless steel, and plastic.

7. The scleral retention apparatus according to claim 2, wherein the inner edge of each of the flanges is adapted to engage and securely hold scleral tissue when said U-shaped member is bent inwardly upon itself.

8. The scleral tissue retention device according to claim 1, wherein the engagement portions comprise a continuous length of deformable material, and the retaining portion comprises selected portions of said engagement portion.

9. The scleral tissue retention device according to claim 1, wherein a engagement portion comprises a length of pliable material capable of being folded upon itself and defining a plurality of openings therethrough, and the retaining portion comprises a length of suture adapted to be threaded through the openings so as to secure said pliable material to underlying scleral tissue.

10. The scleral tissue retention device according to claim 1, wherein the engagement portions comprise pins adapted for insertion into tunnels formed in said scleral tissue, and the retention portion comprises at least one length of suture adapted to tie said pins together.

11. A system for retaining scleral tissue, comprising:
    a scleral tissue retention device comprising:
        first and second engagement portions for respectively engaging first and second spaced portions of the sclera of an eye; each of the engagement portions defining an edge complementarily curved relative to the exterior scleral surface; and
        retaining portion connected to the engagement portions, for holding said first and second engagement portions in close proximity to one another such that two layers of the sclera can be retained therebetween when the retaining portion; and
    an emplacement tool, said emplacement tool comprising;
        a shaft having a proximal end and a distal end;
        a locating portion at said distal end of said shaft adapted for holding and selectively crimping at least part of the retention portion of the retention device; and
        activation apparatus at the proximal end of the shaft connected to the location portion for selectively activating the location portion so as to crimp the retention portion.

12. A method of retaining multiple layers of scleral tissue in abutting relation to one another, the method comprising:
    a) providing a scleral tissue retention device comprising:
        first and second engagement portions for respectively engaging first and second spaced portions of the sclera of an eye; and
        a retaining portion for holding the first and second engagement portions such that two layers of the sclera of the eye can be retained therebetween; and
    b) disposing the engagement portions on opposed sides of a pair of layers of scleral tissue.

13. A method of retaining multiple layers of scleral tissue in tightly abutting relation to one another, the method comprising:
    providing a scleral tissue retention device comprising:
        first and second engagement portions for respectively engaging first and second spaced portions of the sclera of an eye; and
        retaining portion for holding said first and second engagement portions in close proximity to one another such that two layers of the sclera of the eye can be retained therebetween; and
    an emplacement tool, comprising;
        a shaft having a proximal end and a distal end;
        locating portion at said distal end of said shaft adapted for holding and selectively crimping at least part of the retention portion of the retention device; and
        activation apparatus connected to the location portion for selectively activating the location portion so as to crimp the retention portion;
    locating a retention device in the locating portion of the emplacement tool;
    disposing the engagement portion on opposite sides of a pair of layers of scleral tissue with the emplacement tool; and
    activating the activation apparatus to cause the locating portion to crimp the retention portion together thereby securing said layers of scleral tissue in abutting relationship with one another.

* * * * *